(12) United States Patent
Bisch et al.

(10) Patent No.: US 8,053,721 B2
(45) Date of Patent: Nov. 8, 2011

(54) PUMP SET AND PUMP WITH ELECTROMAGNETIC RADIATION OPERATED INTERLOCK

(75) Inventors: Michael E. Bisch, Kirkwood, MO (US); Jeffrey E. Price, Wildwood, MO (US); Gary J. Waldhoff, Maryland Heights, MO (US); Jeffrey E. Forrest, Collinsville, IL (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/494,040

(22) Filed: Jun. 29, 2009

(65) Prior Publication Data

US 2009/0264824 A1    Oct. 22, 2009

Related U.S. Application Data

(63) Continuation of application No. 11/609,234, filed on Dec. 11, 2006, now Pat. No. 7,560,686.

(51) Int. Cl.
*G01D 5/34* (2006.01)

(52) U.S. Cl. .......... 250/231.1; 604/67; 604/141

(58) Field of Classification Search ........... 250/208.1, 250/206, 214 R, 214.1, 214, 231.1; 604/140–141, 604/65, 67, 151–156; 347/84–86, 19
See application file for complete search history.

(56) References Cited

U.S. PATENT DOCUMENTS

| | | | |
|---|---|---|---|
| 2,483,924 A | 10/1949 | Moulinier | |
| 3,432,128 A | 3/1969 | Elleboudt | |
| 3,435,209 A | 3/1969 | Keahl | |
| 3,523,179 A | 8/1970 | Edwards et al. | |
| 3,673,476 A | 6/1972 | Hamburg | |
| 3,675,653 A | 7/1972 | Crowley et al. | |
| 3,693,025 A | 9/1972 | Brunton | |
| 3,851,976 A | 12/1974 | Meier | |
| 3,982,162 A | 9/1976 | Olliffe | |
| 3,985,133 A | 10/1976 | Jenkins et al. | |

(Continued)

FOREIGN PATENT DOCUMENTS

DE    3627011 A1    2/1988

(Continued)

OTHER PUBLICATIONS

Extended European Search Report regarding 07122899.3, dated Apr. 14, 2008, 7 pages.

(Continued)

*Primary Examiner* — Francis M Legasse, Jr.
(74) *Attorney, Agent, or Firm* — Elias Domingo

(57) ABSTRACT

A medical pump including an electromagnetic emitter and detector is provided. The emitter emits electromagnetic radiation of a predetermined wavelength. A pump set that is compatible with the medical pump modifies the emitted electromagnetic radiation when properly installed in the pump. The detector receives electromagnetic radiation, and a filter circuit excludes electromagnetic radiation having a wavelength other than the predetermined wavelength. The pump monitors the filtered signal to determine whether the received electromagnetic radiation corresponds to the emitted electromagnetic radiation as modified by a properly loaded, compatible pump set and determines whether a compatible pump set is properly loaded in the pump as a function thereof.

17 Claims, 12 Drawing Sheets

U.S. PATENT DOCUMENTS

| | | |
|---|---|---|
| 3,987,303 A | 10/1976 | Stoft et al. |
| 3,993,061 A | 11/1976 | O'Leary |
| 4,038,982 A | 8/1977 | Burke et al. |
| 4,126,132 A | 11/1978 | Portner et al. |
| 4,300,048 A | 11/1981 | Barbier et al. |
| 4,346,296 A | 8/1982 | Passaro et al. |
| 4,424,011 A | 1/1984 | O'Brien et al. |
| 4,454,763 A | 6/1984 | Mahler |
| 4,504,263 A | 3/1985 | Steuer et al. |
| 4,508,422 A | 4/1985 | Karlsson |
| 4,525,069 A | 6/1985 | Tanaka et al. |
| 4,537,561 A | 8/1985 | Xanthopoulos |
| 4,646,144 A | 2/1987 | Ishida et al. |
| 4,652,260 A | 3/1987 | Fenton, Jr. et al. |
| 4,665,391 A | 5/1987 | Spani |
| 4,714,463 A | 12/1987 | Archibald et al. |
| 4,720,636 A | 1/1988 | Benner, Jr. |
| 4,763,032 A | 8/1988 | Bramm et al. |
| 4,785,322 A | 11/1988 | Harrison et al. |
| 4,788,444 A | 11/1988 | Williams |
| 4,792,424 A | 12/1988 | Loman |
| 4,797,655 A | 1/1989 | Orndal et al. |
| 4,806,751 A | 2/1989 | Abe et al. |
| 4,845,487 A | 7/1989 | Frantz et al. |
| 4,845,489 A | 7/1989 | Hormel |
| 4,850,807 A | 7/1989 | Frantz |
| 4,878,896 A | 11/1989 | Garrison et al. |
| 4,882,575 A | 11/1989 | Kawahara |
| 4,884,013 A | 11/1989 | Jackson et al. |
| 4,884,065 A | 11/1989 | Crouse et al. |
| 4,909,797 A | 3/1990 | Timothy |
| 4,913,703 A | 4/1990 | Pasqualucci et al. |
| 4,933,563 A | 6/1990 | Thus |
| 4,940,050 A | 7/1990 | Forssmann et al. |
| 4,944,748 A | 7/1990 | Bramm et al. |
| 4,945,244 A | 7/1990 | Castleman |
| 4,950,235 A | 8/1990 | Slate et al. |
| 4,958,910 A | 9/1990 | Taylor et al. |
| 4,976,590 A | 12/1990 | Baldwin |
| 5,055,001 A | 10/1991 | Natwick et al. |
| 5,057,081 A | 10/1991 | Sunderland et al. |
| 5,058,970 A | 10/1991 | Schildkraut et al. |
| 5,101,711 A | 4/1992 | Durbin |
| 5,181,842 A | 1/1993 | Sunderland et al. |
| 5,207,645 A | 5/1993 | Ross et al. |
| 5,211,626 A | 5/1993 | Frank et al. |
| 5,237,450 A | 8/1993 | Stromberg |
| 5,250,027 A | 10/1993 | Lewis et al. |
| 5,256,155 A | 10/1993 | Yerlikaya et al. |
| 5,330,431 A | 7/1994 | Herskowitz |
| 5,336,174 A | 8/1994 | Daoud et al. |
| 5,352,364 A | 10/1994 | Kruger et al. |
| 5,357,113 A | 10/1994 | Liston et al. |
| 5,364,364 A | 11/1994 | Kasvikis et al. |
| 5,415,641 A | 5/1995 | Yerlikaya et al. |
| 5,433,588 A | 7/1995 | Monk et al. |
| 5,436,455 A | 7/1995 | Rosenthal et al. |
| 5,437,635 A | 8/1995 | Fields et al. |
| 5,502,111 A | 3/1996 | Huynh-Ba |
| 5,508,521 A | 4/1996 | Kraft et al. |
| 5,531,680 A | 7/1996 | Dumas et al. |
| 5,531,697 A | 7/1996 | Olsen et al. |
| 5,533,453 A | 7/1996 | Wolfberg et al. |
| 5,536,935 A | 7/1996 | Klotzsch et al. |
| 5,560,355 A | 10/1996 | Merchant et al. |
| 5,567,120 A | 10/1996 | Hungerford et al. |
| 5,569,026 A | 10/1996 | Novak |
| 5,575,284 A | 11/1996 | Athan et al. |
| 5,584,671 A | 12/1996 | Schweitzer, Jr. et al. |
| 5,586,567 A | 12/1996 | Smith et al. |
| 5,602,664 A | 2/1997 | Doyle |
| 5,604,020 A | 2/1997 | Fitchmun |
| 5,620,312 A | 4/1997 | Hyman et al. |
| 5,623,907 A | 4/1997 | Cotton et al. |
| 5,626,129 A | 5/1997 | Klimm et al. |
| 5,631,730 A | 5/1997 | Chupp et al. |
| 5,634,907 A | 6/1997 | Rani et al. |
| 5,661,231 A | 8/1997 | Koskela |
| 5,681,284 A | 10/1997 | Herskowitz |
| 5,683,367 A | 11/1997 | Jordan et al. |
| 5,704,912 A | 1/1998 | Lawrence et al. |
| 5,711,654 A | 1/1998 | Afflerbaugh |
| 5,721,430 A | 2/1998 | Wong |
| 5,741,232 A | 4/1998 | Reilly et al. |
| 5,752,813 A | 5/1998 | Tyner et al. |
| 5,767,976 A | 6/1998 | Ankerhold et al. |
| 5,788,674 A | 8/1998 | McWilliams |
| 5,795,327 A | 8/1998 | Wilson et al. |
| 5,798,699 A | 8/1998 | Bryant et al. |
| 5,818,049 A | 10/1998 | Bailey et al. |
| 5,828,458 A | 10/1998 | Taylor et al. |
| 5,851,631 A | 12/1998 | Borden et al. |
| 5,853,386 A | 12/1998 | Davis et al. |
| 5,882,338 A | 3/1999 | Gray |
| 5,903,006 A | 5/1999 | Kiuchi et al. |
| 5,920,018 A | 7/1999 | Wilkerson et al. |
| 6,013,020 A | 1/2000 | Meloul et al. |
| 6,015,272 A | 1/2000 | Antaki et al. |
| 6,023,970 A | 2/2000 | Blaine |
| 6,067,463 A | 5/2000 | Jeng et al. |
| 6,078,042 A | 6/2000 | Fellows |
| 6,095,986 A | 8/2000 | Braig et al. |
| 6,099,502 A | 8/2000 | Duchon et al. |
| 6,106,498 A | 8/2000 | Friedli et al. |
| 6,117,115 A | 9/2000 | Hill et al. |
| 6,129,699 A | 10/2000 | Haight et al. |
| 6,162,183 A | 12/2000 | Hoover |
| 6,219,138 B1 | 4/2001 | Swanson et al. |
| 6,227,817 B1 | 5/2001 | Paden |
| 6,244,835 B1 | 6/2001 | Antaki et al. |
| 6,263,227 B1 | 7/2001 | Boggett et al. |
| 6,299,600 B1 | 10/2001 | Masaoka et al. |
| 6,325,422 B1 | 12/2001 | Verkaart et al. |
| 6,390,590 B1 | 5/2002 | Hansburg |
| 6,437,316 B1 | 8/2002 | Colman et al. |
| 6,461,323 B2 | 10/2002 | Fowler et al. |
| 6,494,692 B1 | 12/2002 | Green |
| 6,523,414 B1 | 2/2003 | Malmstrom et al. |
| 6,528,791 B1 | 3/2003 | Williams et al. |
| 6,531,708 B1 | 3/2003 | Malmstrom et al. |
| 6,552,145 B1 | 4/2003 | Okada et al. |
| 6,585,684 B1 | 7/2003 | Hughett et al. |
| 6,617,175 B1 | 9/2003 | Arno |
| 6,626,862 B1 | 9/2003 | Duchon et al. |
| 6,659,976 B2 | 12/2003 | Beck et al. |
| 6,661,482 B2 | 12/2003 | Hara |
| 6,683,679 B2 | 1/2004 | Belenkii |
| 6,747,276 B2 | 6/2004 | Watanabe |
| 6,786,879 B1 | 9/2004 | Bolam et al. |
| 6,811,382 B2 | 11/2004 | Buchanan et al. |
| 6,890,291 B2 | 5/2005 | Robinson et al. |
| 6,891,343 B2 | 5/2005 | Petersen |
| 6,900,449 B2 * | 5/2005 | Bolash et al. ............ 250/559.16 |
| 6,949,066 B2 | 9/2005 | Bearnson et al. |
| 6,958,053 B1 | 10/2005 | Reilly |
| 7,009,150 B2 | 3/2006 | Wennemann et al. |
| 7,018,363 B2 | 3/2006 | Cowan et al. |
| 7,041,082 B2 | 5/2006 | Blomquist et al. |
| 7,092,796 B2 | 8/2006 | Vanderveen |
| 7,126,495 B2 | 10/2006 | Netzer |
| 7,144,384 B2 | 12/2006 | Gorman et al. |
| 7,145,127 B2 | 12/2006 | Chin et al. |
| 7,258,534 B2 | 8/2007 | Fathallah et al. |
| 7,462,170 B2 | 12/2008 | Fournie et al. |
| 7,537,579 B2 | 5/2009 | Price |
| 7,560,686 B2 | 7/2009 | Bisch et al. |
| 7,570,428 B2 | 8/2009 | Watanabe |
| 7,591,980 B2 | 9/2009 | Call et al. |
| 7,763,005 B2 | 7/2010 | Knauper et al. |
| 2002/0036276 A1 | 3/2002 | Seeman |
| 2004/0036273 A1 | 2/2004 | McClary |
| 2004/0097872 A1 | 5/2004 | Delk et al. |
| 2004/0158205 A1 | 8/2004 | Savage |
| 2005/0186377 A1 | 8/2005 | Hurst et al. |
| 2005/0214131 A1 | 9/2005 | Miles et al. |
| 2005/0267439 A1 | 12/2005 | Harr et al. |
| 2007/0208304 A1 | 9/2007 | Hudson et al. |

| | | | |
|---|---|---|---|
| 2007/0208305 A1 | 9/2007 | Wiesner et al. | |
| 2007/0208306 A1 | 9/2007 | Harr et al. | |
| 2007/0253833 A1 | 11/2007 | Hanlon et al. | |
| 2008/0147008 A1 | 6/2008 | Lewis et al. | |
| 2009/0284603 A1 | 11/2009 | Hsieh | |

FOREIGN PATENT DOCUMENTS

| | | |
|---|---|---|
| DE | 3910250 A1 | 10/1990 |
| EP | 0467805 B1 | 3/1995 |
| EP | 0563351 B1 | 12/1997 |
| EP | 0718006 B1 | 3/1999 |
| EP | 0891784 B1 | 9/2003 |
| EP | 0876825 B1 | 2/2005 |
| ES | 8500067 A1 | 1/1985 |
| GB | 2065916 A | 7/1981 |
| JP | 2006233014 A | 9/2006 |
| WO | 9320440 A1 | 10/1993 |
| WO | 9320441 A1 | 10/1993 |
| WO | 9508774 A2 | 3/1995 |
| WO | 9844320 A1 | 10/1998 |
| WO | 2004028595 A1 | 4/2004 |

OTHER PUBLICATIONS

Garcia, et al: "Computational Prediction of PVC Degradation During Injection Molding in a Rectangular Channel", Polymer Engineering & Science, Jul. 2004, vol. 44, No. 7, pp. 1295-1312, Society of Plastics Engineers, United States.

Office action dated Aug. 29, 2008 from related U.S. Appl. No. 11/609,234, 16 pgs.

Response filed Jan. 9, 2009 to Office action dated Aug. 29, 2008 in related U.S. Appl. No. 11/609,234, 10 pages.

Compat Yset consisting of four photographs and description, publication date unknown but admitted as prior art, 5 pgs.

European Search Report regarding related application serial No. EP 10172312.0 dated Oct. 15, 2010, 7 pgs.

* cited by examiner

PUMP SET AND PUMP WITH ELECTROMAGNETIC RADIATION OPERATED INTERLOCK

CROSS REFERENCE TO RELATED APPLICATION

This application claims priority from U.S. application Ser. No. 11/609,234, filed on Dec. 11, 2006, the contents of which are incorporated herein by reference in their entirety.

BACKGROUND

Administering fluids containing medicine or nutrition to a patient is well known in the art. Although fluids can sometimes be delivered to the patient by gravity flow, often a flow control apparatus, such as a peristaltic pump or the like, drives a pump set for delivering fluid to the patient at a controlled rate of delivery. A peristaltic pump suitable for use in administering fluids to a patient typically comprises a housing that includes at least one motor operatively engaged to a pump rotor through a gearbox. The motor is operatively connected to a rotatable shaft that drives the pump rotor, which in turn progressively compresses the tubing of the pump set. The peristaltic action effected by rotation of the pump rotor by the motor drives fluid through the tubing. A controller operates the motor, or motors, to drive the pump rotor and, thus, controls fluid flow. Other types of peristaltic pumps not employing pump rotors are also known.

In order for the pump to deliver a precise amount of fluid corresponding with flow parameters programmed into the pump controller, the pump set must be compatible with the pump and correctly loaded in the pump. For example, if the pump set is misaligned in the pump or is not compatible with the pump, the pump may deliver an inaccurate amount of fluid to a patient or generate a low flow alarm requiring the condition to be examined and the set reloaded or changed. Existing pumps have systems to detect whether the pump set is properly loaded. An example of such a pump having a detection system is shown in co-assigned U.S. Pat. No. 4,913,703, entitled SAFETY INTERLOCK SYSTEM FOR MEDICAL FLUID PUMPS, the entire disclosure of which is incorporated herein by reference. In this system, circuitry in the pump detects a magnet on the pump set to determine if it is compatible. Unfortunately, the use of a magnet adds to the cost and complexity of the pump set. Detecting a compatible pump set by use of electromagnetic radiation emitters and detectors is another solution, but ambient electromagnetic radiation from the sun and artificial light sources can interfere with accurately detecting emitted electromagnetic radiation signals.

SUMMARY

Aspects of the invention permit detecting whether a compatible pump set is properly loaded in the presence of electromagnetic radiation interference. One aspect is directed to a medical pump for pumping fluid through a pump set loaded in the medical pump. The pump set is adapted to modify electromagnetic radiation transmitted through the pump set when it is properly loaded in the medical pump. The medical pump includes an emitter, a detector, a filter circuit, and a controller. The emitter emits electromagnetic radiation having a predetermined wavelength, and the detector receives electromagnetic radiation and provides a detector signal representative of the received electromagnetic radiation. The electromagnetic radiation received by the detector includes the electromagnetic radiation having the predetermined wavelength emitted by the emitter and electromagnetic radiation having at least one wavelength other than the predetermined wavelength. The filter circuit filters the detector signal provided by the detector to exclude a portion of the detector signal representative of electromagnetic radiation having a wavelength other than the predetermined wavelength, and provides an output signal representative of the filtered detector signal. The pump controller determines whether a compatible pump set is properly loaded in the medical pump as a function of the output signal and is configured to enable the medical pump for pumping when the compatible pump set is properly loaded in the medical pump as indicated by the output signal.

A method of determining whether a compatible pump set is properly loaded in a medical pump embodies further aspects. A compatible pump set modifies electromagnetic radiation transmitted through the pump set when it is properly loaded in the medical pump. An emitter of the medical pump emits pulses of electromagnetic radiation having a predetermined wavelength at a predetermined frequency through a portion of a pump set loaded in the medical pump. A detector of the medical pump receives electromagnetic radiation including electromagnetic radiation. The received electromagnetic radiation includes electromagnetic radiation having the predetermined wavelength and electromagnetic radiation having at least one wavelength other than the predetermined wavelength. In turn, the detector provides a detector signal representative of the received electromagnetic radiation. According to the method, a filter circuit filters the detector signal to exclude frequencies other than the predetermined frequency of the pulses of electromagnetic radiation having the predetermined wavelength and provides an output signal representative of the intensity of the electromagnetic radiation pulsed at the predetermined frequency received by the detector. The method also includes comparing the output signal to a threshold to determine whether the emitted electromagnetic radiation transmitted through the pump has been modified, generating a detection signal representative of the comparison, and determining whether the pump set is compatible with the medical pump and properly loaded in the medical pump as a function of the detection signal.

A method of detecting electromagnetic radiation having a predetermined wavelength pulsed at a predetermined frequency in the presence of ambient light embodies yet further aspects. The method is for use with a medical pump, which includes an emitter for emitting electromagnetic radiation having the predetermined wavelength and a detector for receiving electromagnetic radiation. The ambient light includes electromagnetic radiation having a plurality of wavelengths. The detector of the medical pump receives electromagnetic radiation and provides a detector signal representative of the received electromagnetic radiation. The received electromagnetic radiation includes the electromagnetic radiation having the predetermined wavelength emitted by the emitter of the pump at the predetermined frequency and the electromagnetic radiation having the plurality of wavelengths. A filter circuit of the pump filters the detector signal to exclude a portion of the detector signal representative of electromagnetic radiation having frequencies other than the predetermined frequency. The filter circuit provides an output signal representative of the electromagnetic radiation having the predetermined frequency received by the detector. The pump compares the output signal to a threshold and generates a detection signal as a function of comparing the output signal to the threshold. When the detection signal exceeds the threshold, the detection signal is digital high and, when the output signal does not exceed the threshold, the detection signal is digital low. The pump determines that the emitted electromagnetic radiation is being received at the detector as a function of the detection signal. That is, the pump determines that the emitted electromagnetic radiation is being received a the detector when the output signal is digital high.

In another aspect, a medical pump pumps fluid through a pump set loaded therein when the pump set is properly loaded in the pump. The pump set modifies electromagnetic radiation transmitted through the pump set by the pump when properly loaded in the medical pump The pump includes an emitter, a detector, a filter circuit, and a controller. The emitter emits pulses of electromagnetic radiation, having a predetermined wavelength at a predetermined frequency. The detector receives electromagnetic radiation and provides a detector signal representative of the received electromagnetic radiation. The electromagnetic radiation received by the detector includes the pulses of electromagnetic radiation having the predetermined wavelength emitted by the emitter and electromagnetic radiation having at least one wavelength other than the predetermined wavelength. The filter circuit filters the detector signal provided by the detector to exclude frequencies other than the predetermined frequency of the pulses of electromagnetic radiation having the predetermined wavelength. The filter circuit provides an output signal representative of the intensity of the electromagnetic radiation pulsed at the predetermined frequency received by the detector. The controller for determines whether a compatible pump set is properly loaded in the pump as a function of the output signal and enables the pump for pumping when the compatible pump set is properly loaded in the pump as indicated by the output signal.

Other aspects are directed to a method of determining whether a compatible pump set is properly loaded in a medical pump. The pump set modifies electromagnetic radiation transmitted through the pump set when properly loaded in the pump. An emitter of the pump emits electromagnetic radiation having a predetermined wavelength through a portion of a pump set loaded in the pump. A detector of the pump receives electromagnetic radiation including electromagnetic radiation having the predetermined wavelength and electromagnetic radiation having wavelengths other than the predetermined wavelength and provides a detector signal representative of the received electromagnetic radiation. A filter circuit of the pump filters the detector signal to exclude a portion of the detector signal representative of the electromagnetic radiation having wavelengths other than the predetermined wavelength and provides an output signal representative of the filtered detector signal. The pump then compares the output signal to a threshold to determine whether the emitted electromagnetic radiation transmitted through the pump set has been modified and generates a detection signal representative of the comparison. The pump determines whether the pump set is compatible with the pump and properly loaded in the pump as a function of the detection signal.

Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

BRIEF DESCRIPTION OF THE DRAWINGS

Corresponding reference characters indicate corresponding parts throughout the several views of the drawings.

DETAILED DESCRIPTION

Figure 1:
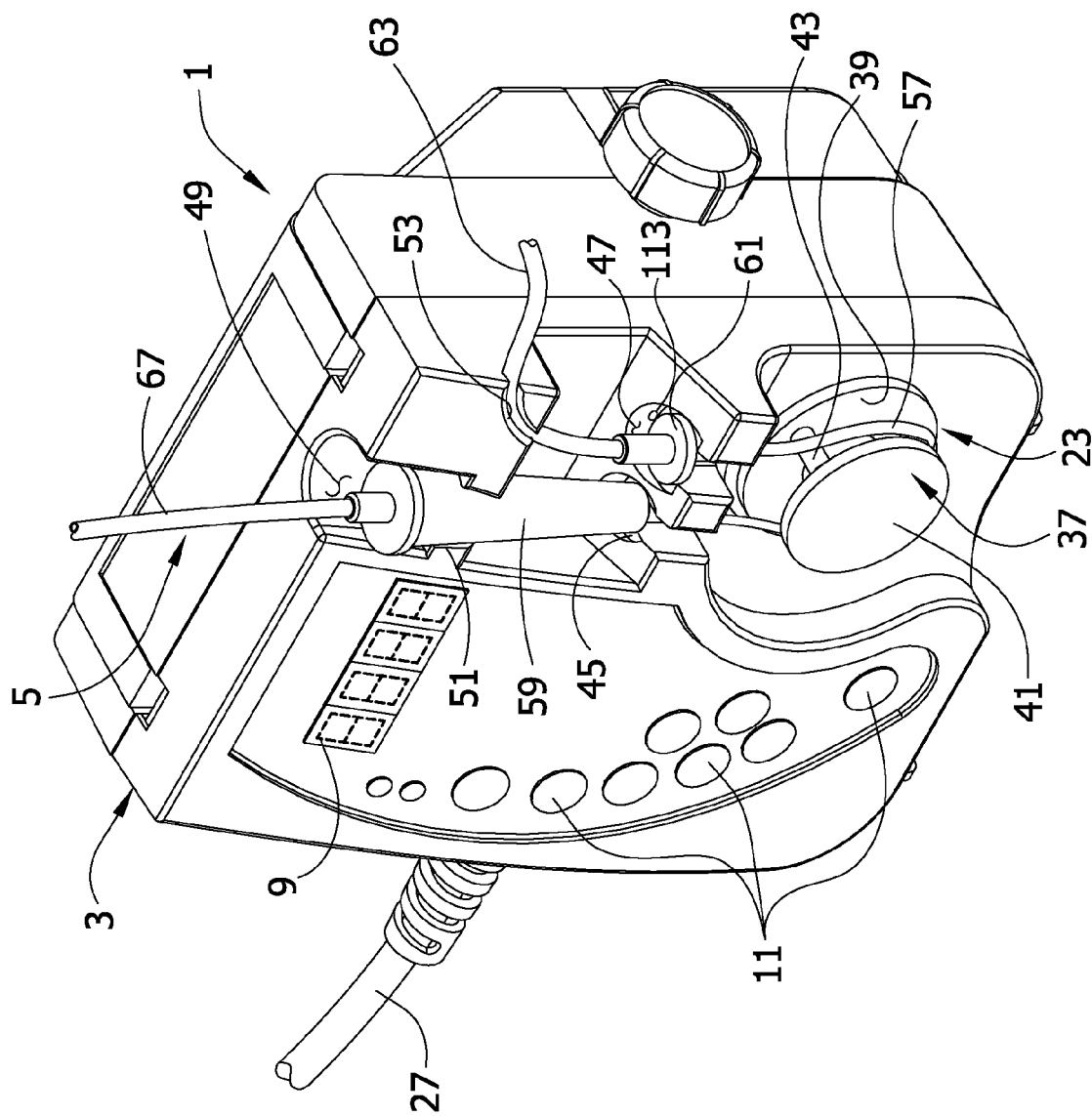
FIG. 1 is a perspective of an enteral feeding pump showing a fragmentary portion of a pump set received on the pump.

Referring now to FIG. 1, an enteral feeding pump (broadly, "a pumping apparatus") constructed according to the principles of the present invention is generally indicated at 1. The feeding pump comprises a housing generally indicated at 3 that is constructed so as to mount a pump set generally indicated at 5 (see FIGS. 1 and 2). It will be appreciated that "housing" as used herein may include many forms of supporting structures (not shown), including without limitation multi-part structures and structures that do not enclose or house the working components of the pump 1. The pump 1 also has a user interface in the form of, for example, a display screen 9 on the front of the housing 3 that is capable of displaying information about the status and/or operation of the pump 1. Buttons 11 on the side of the display screen 9 are provided for use in controlling and obtaining information from the pump 1. It will be understood that although the illustrated pump 1 is a rotary peristaltic enteral feeding pump, the present invention has application to other types of pumps (not shown), including medical infusion pumps, adapted for receiving a pump set. A pump of the same general type as described herein is shown in co-assigned U.S. Pat. No. 4,909,797 entitled ENTERAL DELIVERY SET WITH SHADED DRIP CHAMBER, the disclosure of which is incorporated herein by reference.

The enteral feeding pump 1 further includes a pumping unit (indicated generally at 23) comprising a pump motor (not shown) located in the housing 3. An electrical cord 27 extends from the housing 3 for connection to a source of electrical power for the motor. Alternatively, or in addition, a battery (not shown) may be received in the housing 3 for powering the pump motor. The pumping unit 23 further includes a pump rotor (generally indicated at 37) mounted on a rotatable shaft (not shown) of the pumping unit. In one embodiment, the pump rotor 37 includes an inner disk 39, an outer disk 41, and three rollers 43 (only one is shown) mounted between the inner and outer disks for rotation about their longitudinal axes relative to the disks. In the illustrated embodiment, the pump motor, rotatable shaft and pump rotor 37 may broadly be considered "a pumping device". The pump housing 3 includes a first lower recess 45 above the pump rotor 37 and a second lower recess 47 generally adjacent the first lower recess. The housing 3 has an upper recess 49 generally axially aligned with the first lower recess 45 and a shoulder 51 at the bottom of the upper recess for receiving and holding part of the pump set 5. A curved recess 53 in the housing 3 above the second lower recess 47 receives and holds another part of the pump set 5 in place. The lower recesses 45, 47, upper recess 49 and curved recess 53 may broadly be considered, individually or as a group, "a receiving portion" of the housing 3 that receives parts of the pump set 5 in a manner that will be described in more detail hereinafter.

Figure 2:
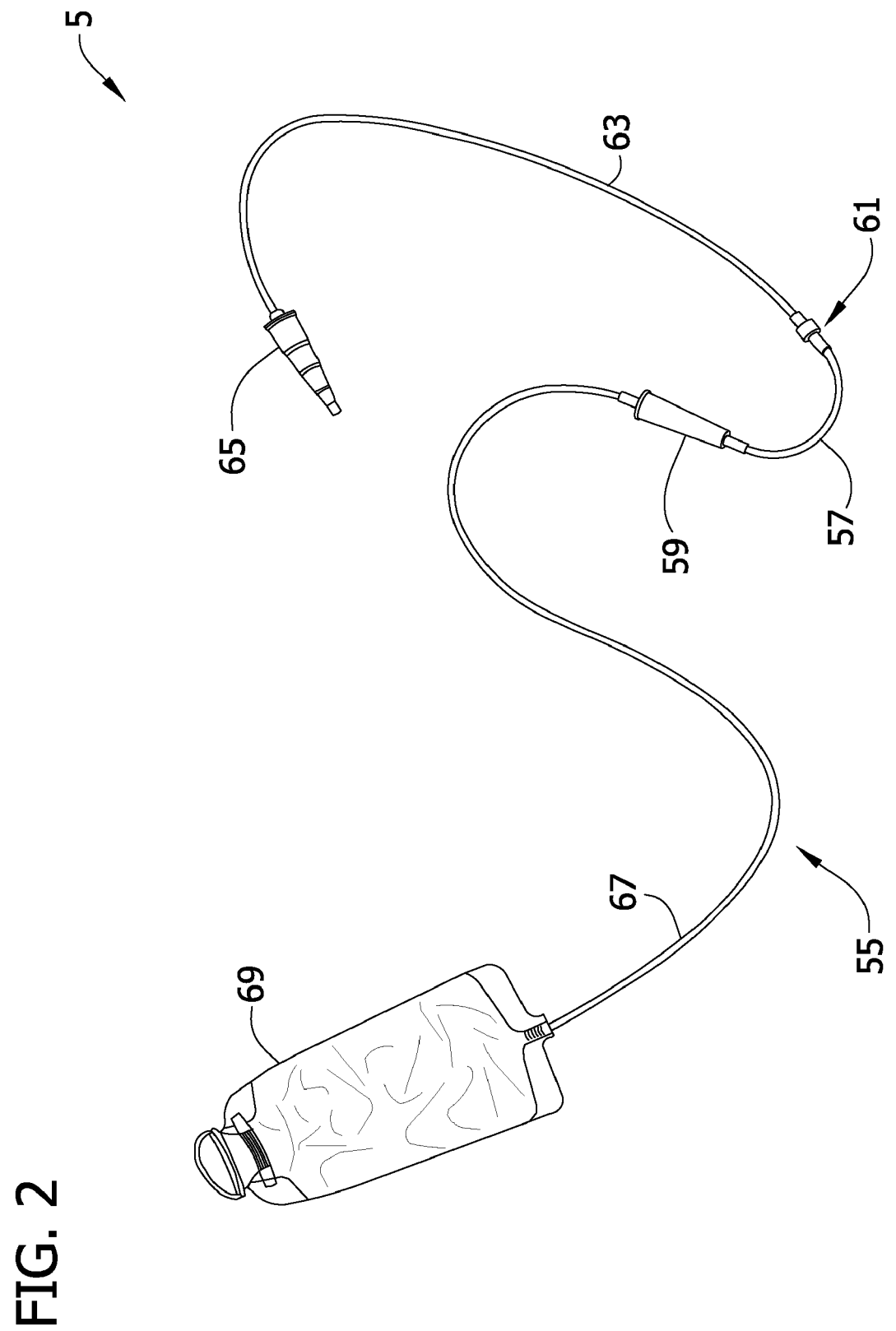
FIG. 2 is an elevation view of the pump set shown in FIG. 1.

Referring now to FIG. 2, the pump set 5 comprises tubing (broadly, "a conduit") indicated generally at 55 that provides a fluid pathway between at least one source of fluid and a patient. Tubing 55 can be made of a medical grade, deformable silicone and comprises a first tube section 57 connected in this embodiment between a drip chamber 59 and a safety interlock device, generally indicated at 61. A second tube section 63 is connected to the safety interlock device 61 and at an outlet of the tubing 55 to a connector, such as a barbed connector 65, suitable for connection to a gastrostomy device (not shown) attached to a patient. A third tube section 67 is connected at an inlet of the tubing 55 to a bag 69 of nutrient liquid and to the drip chamber 59. As previously stated, pump sets of different constructions may be used, for example a recertification set (not shown) may be used to verify and/or correct pumping accuracy. The pump 1 can be configured to automatically recognize what kind of set is installed and to alter its operation to conform to that called for by the particular pump set. Still further, the pump 1 can be configured to detect with sensors whether the first tube section 57 is properly installed on the pump.

Figure 3:
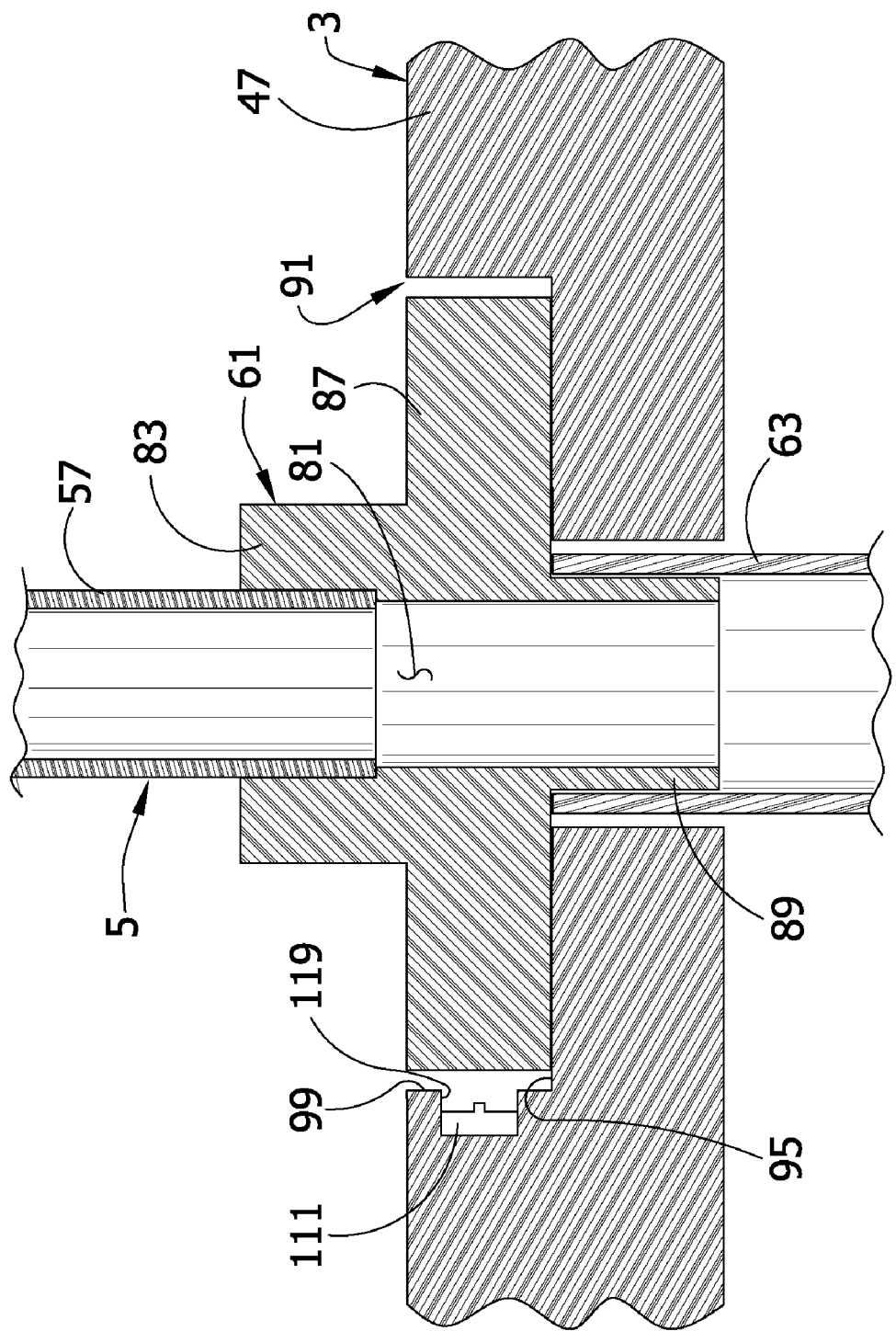
FIG. 3 is an enlarged, fragmentary section of the pump shown in FIG. 1 and the safety interlock device embodying aspects of the invention.

Referring to FIG. 3, a cross section of the safety interlock device 61 and a portion of the housing 3 that receives the safety interlock device 61 is shown. The safety interlock device 61 connects the first tube section 57 and the second tube section 63 of the pump set 5 and has a central axial bore 81 to allow the flow of fluid between the first tube section 57 and the second tube section 63. The safety interlock device 61 has an upper cylindrical portion 83 that receives a portion of the first tube section 57, an electromagnetic radiation propagation affecting member 87 that extends radially outward from the upper cylindrical portion 83, and a lower cylindrical portion 89 that is received in the second tube section 63 for attaching the second tube section 63 to the safety interlock device 61. It is to be understood that the safety interlock device 61, and in particular the member 87 may be separate from the pump set 5, and/or may be attached to the pump set 5 in such a way that liquid does not pass through the safety interlock device 61. The electromagnetic radiation propagation affecting member 87 is sized to be received on a seat, indicated generally at 91, formed at the bottom of the second lower recess 47 in the pump 1 when the pump set 5 is properly loaded on the pump 1. In the illustrated embodiment, the seat 91 is generally semi-cylindrical to correspond with the shape of the safety interlock device 61 and includes an axially facing surface 95 in the second lower recess 47 and a radially facing surface 99 in the second lower recess 47.

In the embodiment of FIG. 3, proper functioning of the pump 1 is generally achieved when the radiation propagation affecting member 87 is seated in substantially face-to-face relation with the axially facing surface 95 of the seat 91. However, the rotation orientation of the member 87, within the seat 91, about its axis is generally not pertinent to operation. Other ways of positioning the propagation affecting member 87 may be used within the scope of the present invention. The safety interlock device 61 and the seat 91 in the housing 3 may be shaped to prevent the pump set 5 from being accidentally dislodged and to prevent the use of incompatible pump sets that do not have the safety interlock device 61. In the illustrated embodiment, the safety interlock device 61 and seat 91 are generally cylindrical in shape but it is understood that other shapes (e.g., hex-shaped) may be used for the safety interlock device 61 and the seat 91. In one embodiment, the safety interlock device 61 is comprised of a material (e.g., a thermoplastic polymer resin such as polysulfone thermoplastic resin or other suitable materials) that is opaque to visible light but easily transmits electromagnetic radiation in the infrared range. It is also contemplated that the safety interlock device 61 may transmit visible light while being opaque to infrared radiation without deviating from the scope of the invention.

Generally speaking, the member 87 of safety interlock device 61 is able to affect the propagation of electromagnetic radiation by diffusion, diffraction, reflection, refraction, and/or blocking, or any combination of diffusion, diffraction, reflection, refraction, and/or blocking. Diffusion is generally understood as the scattering of electromagnetic radiation rays either when reflected from a rough surface or during transmission of electromagnetic radiation through a translucent medium. Diffraction is generally understood as the bending of electromagnetic radiation rays around the edges of opaque objects. Reflection is understood as the return or change in the direction of travel of particles or radiant energy which impinges on a surface but does not substantially enter the substance providing the reflecting surface. Refraction is understood as the change in direction of motion of a ray of radiant energy as it passes obliquely from one medium into another in which the speeds of propagation are different (e.g., media of different densities). The amount of refraction is based on the index of refraction dependent in part on the density of the material facing the medium. Blocking is understood to mean substantially impeding electromagnetic radiation rays from traveling through a medium.

Figure 4:
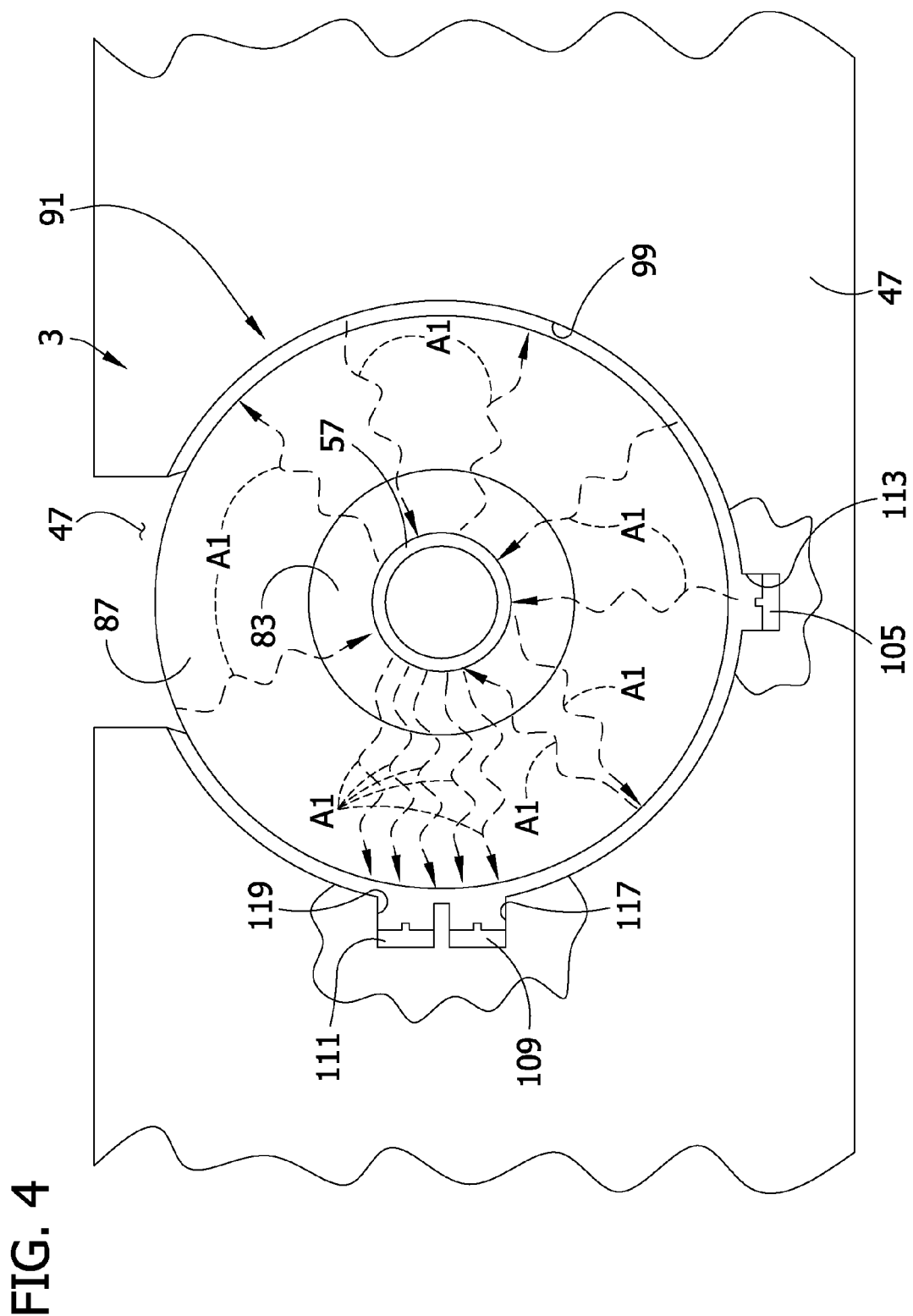
FIG. 4 is a top plan view of FIG. 3.

Referring to FIG. 4, the IR emitter 105 is positioned in an alcove 113 in the second lower recess 47 of the housing 3 so that electromagnetic radiation (indicated by arrows A1 in FIG. 4) from the emitter is directed to the electromagnetic radiation propagation affecting member 87 of the safety interlock device 61 (see also, FIG. 3). When the compatible pump set 5 is properly loaded and, consequently, safety interlock device 61 is properly located on the seat 91, the infrared radiation from the IR emitter 105 is diffused through the electromagnetic radiation propagation affecting member 87 and internally reflected so that the infrared radiation is directed to and received by the IR detector 109. Diffusion may be enhanced by the addition of particulates to the material of the member 87. In this embodiment, the infrared radiation propagation is affected primarily through internal reflection. Other effects on infrared radiation propagation, such as diffusion, may also assist. However, any infrared radiation that is refracted is minimal and does not contribute to the infrared radiation signal seen by the IR detector 109 (i.e., refraction causes a reduction in signal strength). The IR detector is positioned in an alcove 117 in the radially facing surface 99 of the seat 91. As described below, a visible light detector 111 may be positioned in an alcove 119. The alcoves 113, 117, 119 recess the IR emitter 105, the IR detector 109, and the visible light detector 111 to protect them from physical contact with the propagation affecting member 87. Although not shown, a clear plastic window may enclose each of the emitter 105 and the detectors 109, 111 within their corresponding alcoves 113, 117, 119 for additional protection. Moreover, the alcoves 117 and 119 help to shield the detectors 109 and 111 from ambient electromagnetic radiation (which may include both visible light and infrared radiation).

In the illustrated embodiment, the IR emitter 105 is located approximately 90 degrees from the IR detector 109. When the pump set 5 is not loaded in the second lower recess 47 and the electromagnetic radiation propagation affecting member 87 is not received on the seat 91, the infrared radiation from the IR emitter 105 is not detected by the IR detector 109. Also when the safety interlock device 61 is not received on the seat 91, visible light from outside of the pump 1 (i.e., ambient light) may enter the second lower recess 47 and is detected by the visible light detector 111. The propagation affecting member 87 is constructed of a material that transmits infrared radiation, but is opaque to visible light. The propagation affecting member 87 may be monolithic or may have other constructions such as an outer layer (not shown) that transmits infrared radiation, but does not transmit visible light and an inner layer or core that is transmissive to both infrared radiation and visible electromagnetic radiation.

Figure 4A:
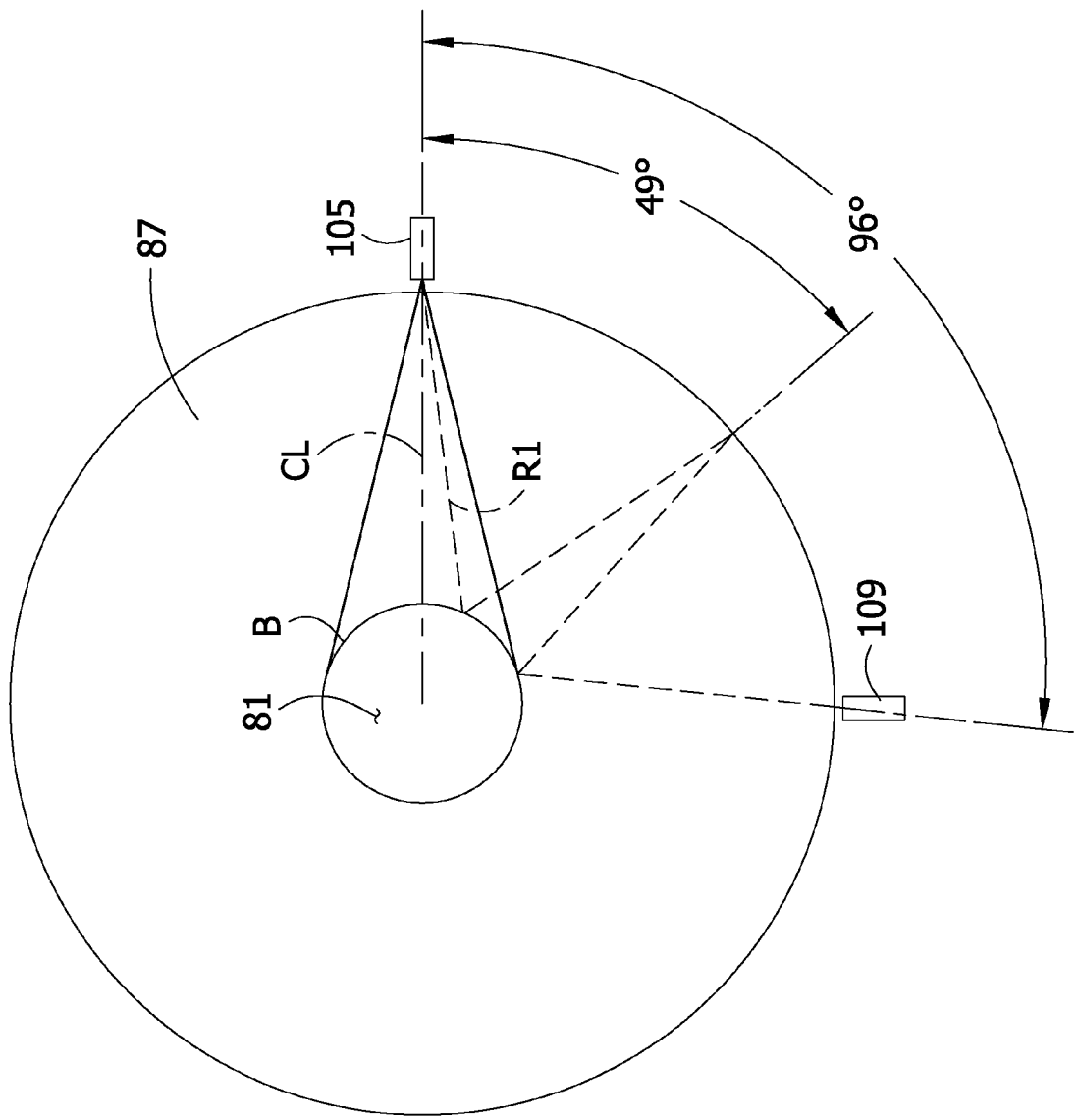
FIG. 4A is a schematic diagram similar to FIG. 4 showing propagation of a light ray in the safety interlock device.

Referring to FIG. 4A, movement of infrared radiation within the electromagnetic radiation propagation affecting member 87 is schematically illustrated. The IR emitter 105 emits infrared radiation in a cone-like pattern toward the side of the member 87. The IR emitter 105 is arranged generally perpendicular to the immediately adjacent side of the member 87. The centerline CL of the cone is denoted in the drawing. For simplicity, we will ignore diffusion and look at a ray R1 of radiation that is a bisector of approximately one half of the cone. The ray R1 is representative of the nominal path of infrared radiation in this half of the cone. The other half of the cone (i.e., that portion above the centerline CL in FIG. 4A) is believed to be of small or no use in providing a light signal capable of being detected by the IR detector 109. The ray R1 in this example strikes the side of the propagation affecting member 87 at an angle so that it enters the member rather than being reflected back. The ray R1 travels generally toward the center of the member 87 until it reaches a boundary B (broadly, "an inner boundary region") around the axial bore 81 of the member. The ray R1 is reflected back toward the side of the member 87 where a good percentage of the ray is reflected back toward the center. At the boundary B, the ray R1 is once more reflected back toward the side of the member 87. Finally, the ray strikes the interior side of the member 87 at a location that is about 96 degrees away from the location of the IR emitter 105. It has been found that a particularly high level of intensity of infrared radiation escapes the member 87 at this location. Accordingly, the IR detector 109 is preferably positioned here, or in a range of around 75-105 degrees. Another higher intensity node is found at a location around 49 degrees from the IR emitter 105, as would be expected from the reflection.

The boundary B of the electromagnetic radiation propagation affecting member 87 can be made of the same material as the remainder of the member. The material at the boundary B may be more "polished" (i.e., more specular) than elsewhere to increase its ability to reflect electromagnetic radiation impinging upon the boundary. However, it is also possible that the central part of the member 87 could be formed of a separate material. In that case, the member 87 would be formed of an inner and an outer member. In use, the pump set feeding fluid bag 69 can be hung from a suitable support, such as an IV pole (not shown). The drip chamber 59 can be placed in the first lower recess 45 and upper recess 49 in an operating position as shown in FIG. 1. The first tube section 57 is placed around the lower part of the pump rotor 37 and the safety interlock device 61 is placed on the seat 91 at the bottom of the second lower recess 47. The seat 91 in the second lower recess 47 is generally located so that the safety interlock device 61 can be placed into the second lower recess 47 at a location in which the first tube section 57 is substantially stretched around the pump rotor 37. The IR emitter 105 and IR detector 109 may intermittently or continuously check for the presence of the properly loaded pump set 5. When the safety interlock device 61 is received in a proper operating position on the seat 91, the infrared signal from the IR emitter 105 is directed to the electromagnetic radiation propagation affecting member 87. The electromagnetic radiation propagation affecting member 87 admits the infrared radiation into its interior where the electromagnetic radiation is diffused and internally reflected (see FIGS. 4 and 4A). Some of the infrared radiation which is redirected outward and impinges the outer boundary of the electromagnetic radiation propagation affecting member 87 substantially at right angles thereto passes out of the electromagnetic radiation propagation affecting member 87. Some of the escaping infrared radiation is directed toward the IR detector 109. The IR detector 109 is periodically operated and detects the presence of infrared radiation when the compatible pump set 5 has been properly loaded on the pump 1. Upon detection of the infrared signal, the IR detector 109 sends a corresponding signal to a controller (e.g., controller 504 in FIG. 6) of the pump 1. Also, when the safety interlock device 61 is loaded onto the seat 91, visible light is blocked by the member 87 from reaching the visible light detector 111. When the pump set 5 is loaded, the visible light detector 111 sends a signal to the controller to indicate that visible light is blocked and the pump 1 may be operated.

Figure 5:
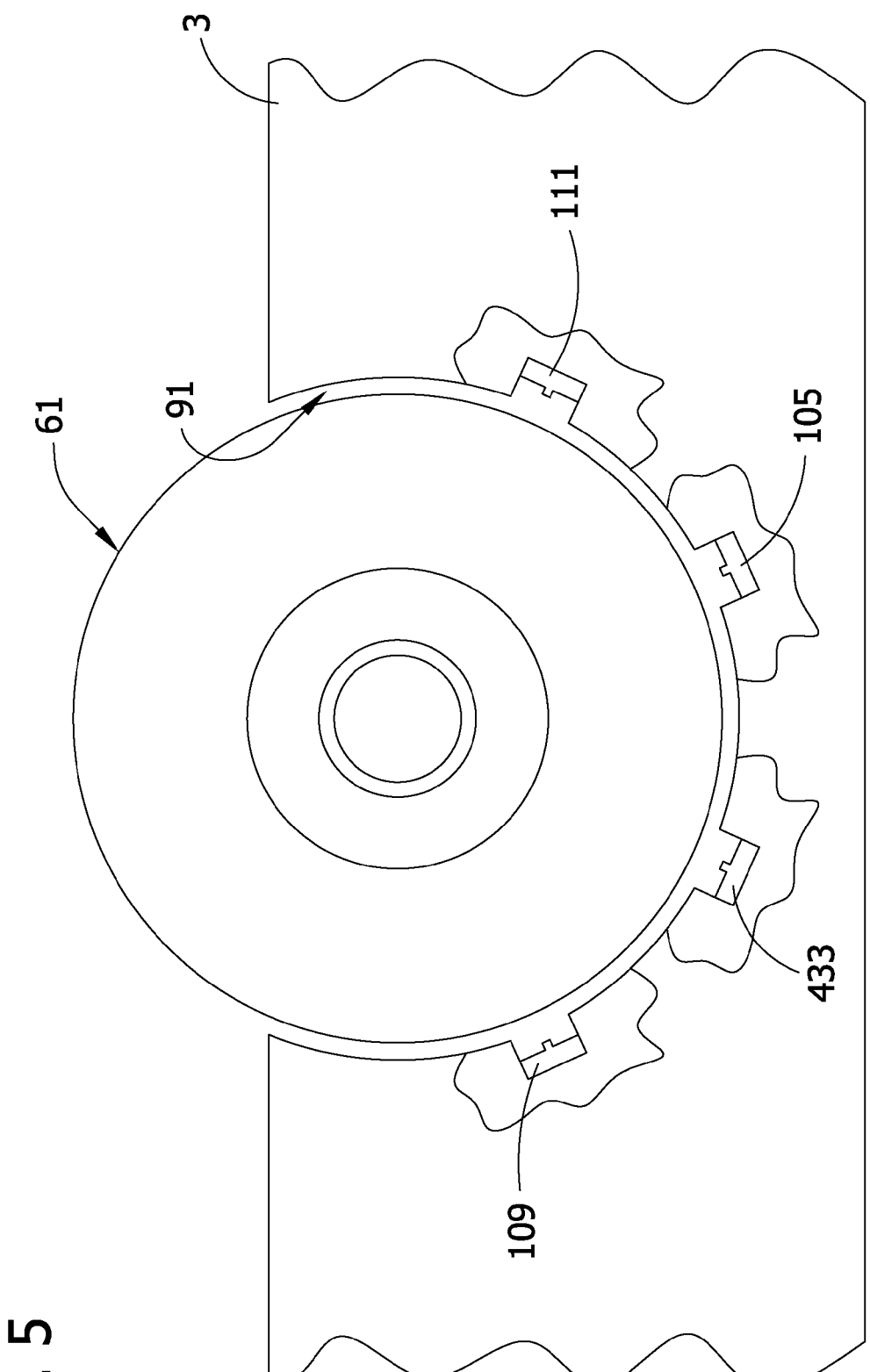
FIG. 5 is a top plan view of a pump and a safety interlock device embodying further aspects of the invention.

FIG. 5 shows a seat 91 and a safety interlock device 61 of another embodiment of the present invention. The embodiment shown in FIG. 5 is similar to the embodiment of FIGS. 4-4A but adds a visible light emitter 433 (e.g., a green light emitting diode). This embodiment includes the IR emitter 105, the IR detector 109, the visible light detector 111, and a visible light emitter 433 in respective alcoves in the housing 3. In this embodiment, the IR emitter 105 and the IR detector 109 are arranged at an approximately 90 degree angle with respect to each other and the visible light emitter 433 and the visible light detector 111 are arranged at an approximately 90 degree angle with respect to each other. Other relative angles are also possible. Generally speaking, the IR detector 109 is located relative to the IR emitter 105 so that in the absence of the safety interlock device 61, the infrared radiation emitted by the IR emitter 105 will not impinge upon the IR detector 109, and the visible light detector 111 is located relative to the visible light emitter 433 so that in the absence of the safety interlock device 61, the visible light emitted by the visible light emitter 433 will impinge upon the visible light detector 111. Both the IR emitter 105 and visible light emitter 433 are arranged generally perpendicular to the immediately adjacent side of the safety interlock device 61 when properly mounted on the pump 1. Moreover in this and other embodiments, the gap between the emitters 105, 433 and the safety interlock device 61 is preferably small in relation to the diameter of the safety interlock device (e.g., nominally 0.005 inches or about 0.13 mm). The safety interlock device 61 of this embodiment is transmissive to infrared radiation but is opaque to visible light. In other words, the interlock device 61 filters out visible light but passes infrared radiation.

In one embodiment, the IR emitter 105 and IR detector 109 are both operated intermittently to detect the presence of the safety interlock device 61 on the seat 91. The IR emitter 105 is operated to generate a pattern of infrared radiation pulses. The IR detector 109 is operated in a series of detector activations or pulses that check for the presence of electromagnetic radiation from the IR emitter 105. Typically, the number of activations from the IR detector 109 will be greater than the number of pulses from the IR emitter 105 for a given period of time. For example, the IR detector 109 may have two activations in a three second time period and the IR emitter 105 may be programmed to generate one pulse of infrared radiation during the three second time period. During the three second time period, the pump 1 has a ratio of detector activations to emitter activations of about 2:1. It is understood that the pump 1 may have other ratios and that the IR emitter 105 and IR detector 109 may operate in other predetermined intermittent patterns without departing from the scope of this invention. The pump 1 may be configured for recognizing a particular, and for example irregular, pattern of activations of the IR emitter 105.

Figure 6:
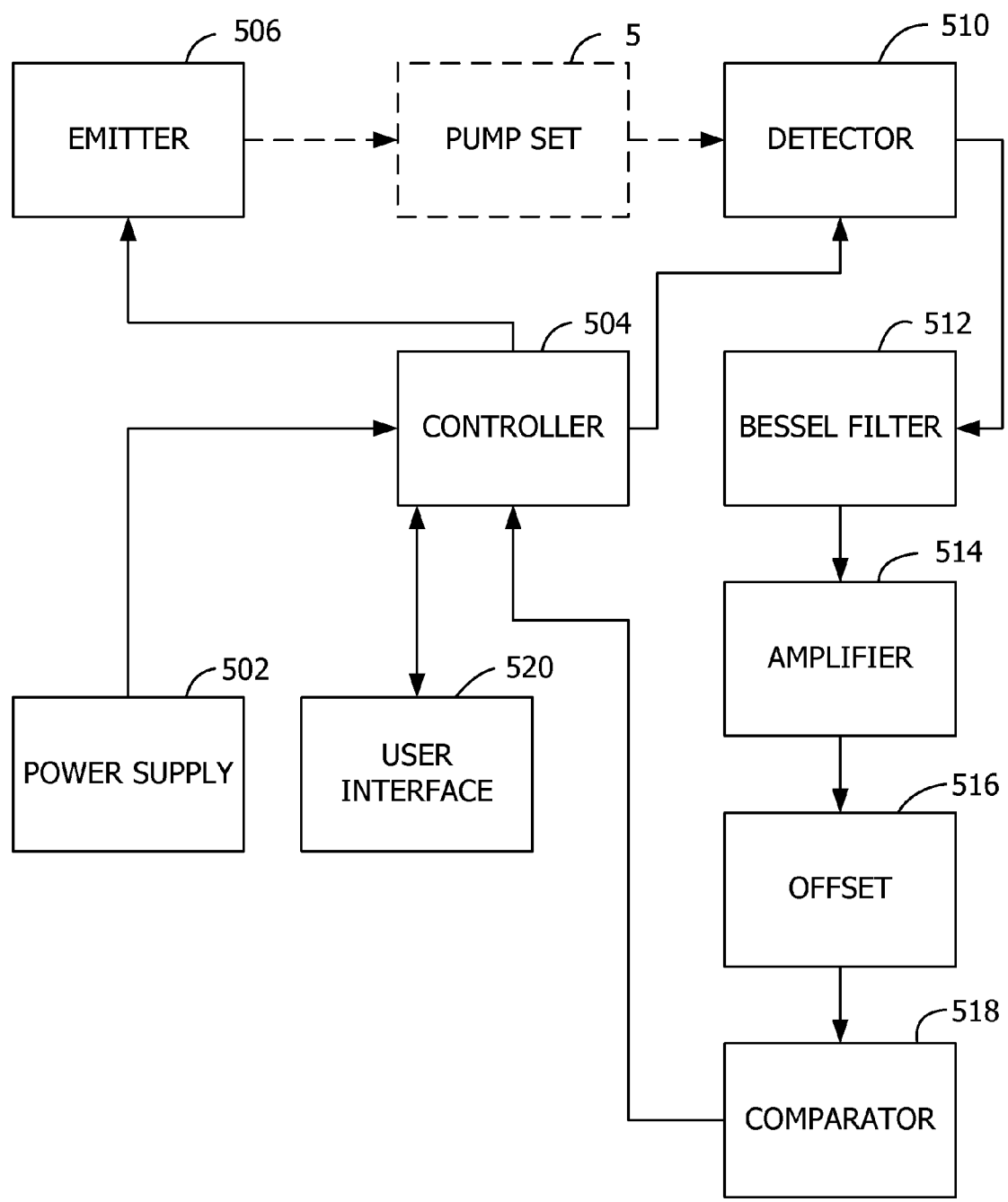
FIG. 6 is an exemplary block diagram of an electromagnetic radiation detection system of the pump.

Referring to FIG. 6, a block diagram of a system for detecting whether the pump set 5 is loaded in the pump 1 is shown according to one embodiment of the invention. A power supply 502 of the pump 1 supplies power to a controller 504 of the pump 1. The controller 504 activates an electromagnetic radiation emitter 506 (e.g. the IR emitter 105 or visible light emitter 433) as described above such that the electromagnetic radiation emitter 506 emits electromagnetic radiation having a predetermined wavelength at a predetermined frequency. A pump set 5 that is compatible with the pump 1 modifies the emitted electromagnetic radiation if it is properly loaded on the pump (i.e., the safety interlock device 61 modifies the emitted electromagnetic radiation when properly installed in the pump 1). A detector 510 (e.g., IR detector 109 and/or visible light detector 111) receives electromagnetic radiation and provides a corresponding detector signal to a filter 512 (e.g. a Bessel or other type bandpass filter). The filter 512 substantially filters out frequencies other than the predetermined frequency and an amplifier 514 amplifies the filtered signal. Those skilled in the art are familiar with a number of suitable circuits for implementing bandpass filters and the like.

Figure 6A:
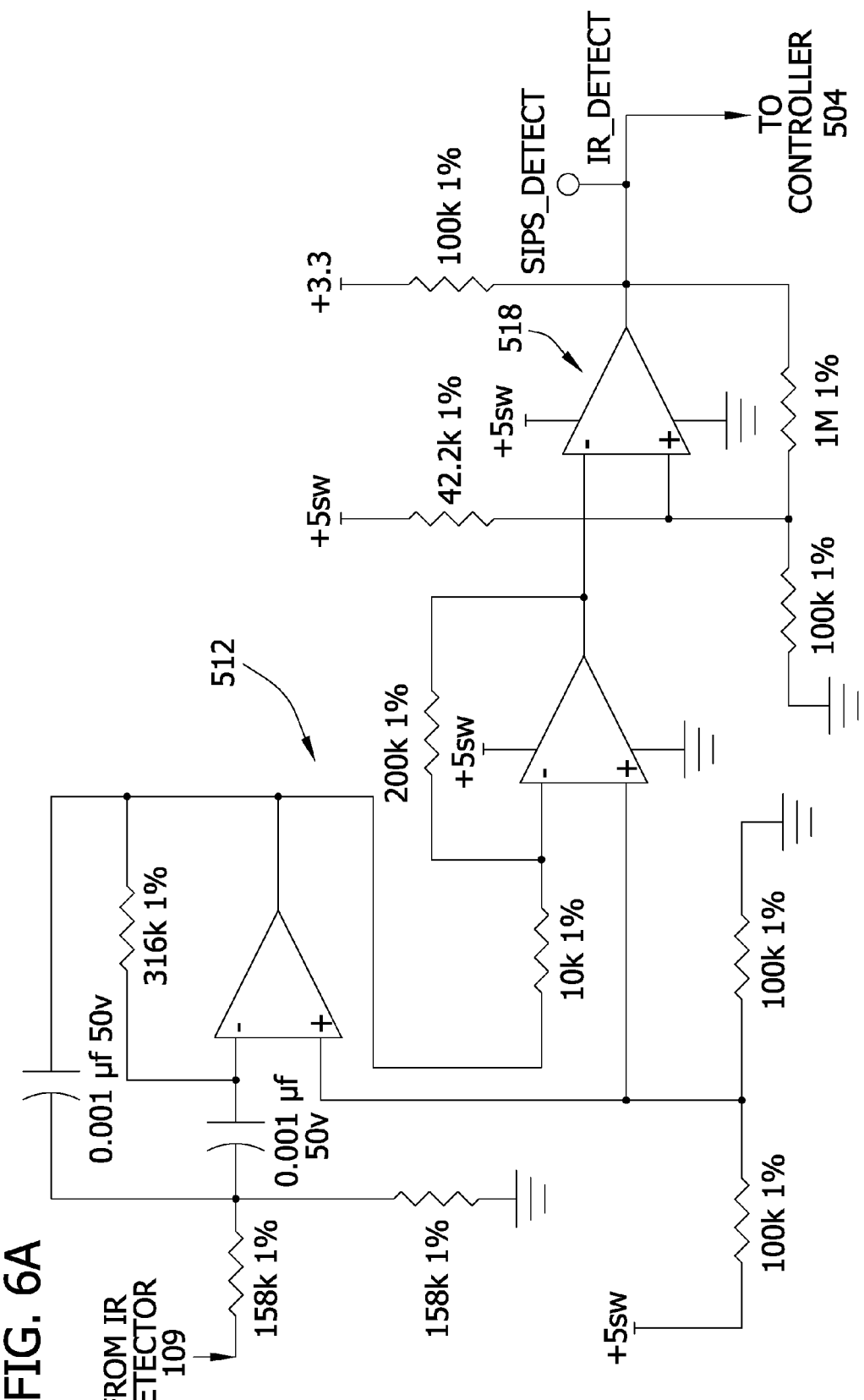
FIG. 6A is an exemplary schematic diagram illustrating aspects of the electromagnetic radiation detection system of FIG. 6.

As shown in FIG. 6, an offset circuit 516 references the signal to a reference point (e.g. ½ of a voltage of the power supply 502) and a comparator 518 compares the offset output signal from the detector and offset circuit to a threshold (e.g., ⅔ of the voltage of the power supply 502). The comparator 518 provides a detection signal to the controller 504 as a function of the comparison. For example, the comparator 518 may provide a digital 'high' signal (e.g. 5 volts) when the offset signal exceeds the threshold and a digital 'low' signal (e.g. 0 volts) when the offset signal does not exceed the threshold. The controller 504 determines whether a pump set that is compatible with the pump 1 is properly loaded in the pump 1 as a function of the detection signal as described above. That is, if the emitted electromagnetic radiation has been modified as if a compatible pump set 5 were properly loaded on the pump 1, the controller 504 determines that a compatible pump set 5 is properly loaded on the pump 1 and enables operation of the pump 1. The controller 504 may warn a user of the pump 1 that a pump set is not loaded via a user interface 520 of the pump 1 such as display screen 9. One skilled in the art will recognize that the filter 512, amplifier 514, offset circuit 516, and comparator 518 may be integrated in the controller 504 or detector 510, or a combination thereof. FIG. 6A illustrates an exemplary circuit for implementing filter 512 and comparator 518.

Figure 7:
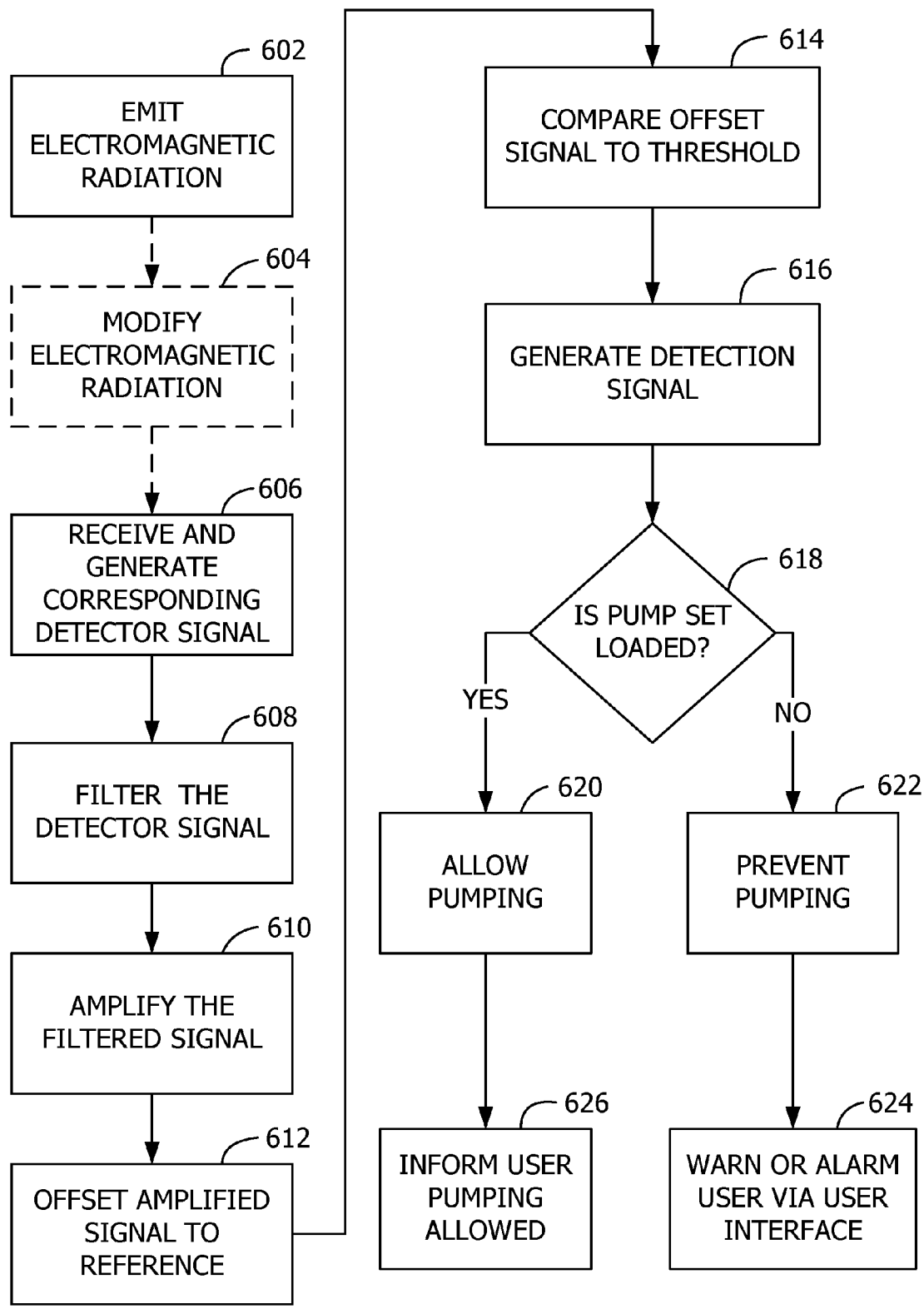
FIG. 7 is an exemplary flow chart illustrating a method of determining whether a pump set is loaded in the pump.

Referring to FIG. 7, a flow chart illustrates an exemplary method of determining whether the compatible pump set 5 fitted with safety interlock device 61 is properly loaded in the pump 1. At 602, the emitter 506 of the pump 1 intermittently emits electromagnetic radiation having a predetermined wavelength (e.g., IR at approximately 880 nanometers) at a predetermined frequency (e.g. 1 kHz). At 604, if a pump set 5 that is compatible with the pump 1 is properly loaded in the pump 1, electromagnetic propagation affecting member 87 will modify the emitted electromagnetic radiation. The pump set 5 may modify the emitted electromagnetic radiation, for example, by blocking the emitted electromagnetic radiation or by conducting the emitted electromagnetic radiation. At 606, the detector 510 receives electromagnetic radiation including electromagnetic radiation having the predetermined wavelength and generates a corresponding detector signal. The detector signal is filtered by a bandpass filter such as a Bessel type bandpass filter at 608, and at 610, an amplifier amplifies the output signal. At 612, an offset circuit references the amplified output signal to a reference such as ½ of the voltage of a power supply of the pump 1, and at 614, a comparator compares the offset output signal to a threshold (e.g., ⅔ of the voltage of the power supply). The reference of ½ of the voltage of the power supply is selected so that the output signal range is not clipped by ground (0 volts) or the maximum voltage of the power supply, and the threshold of ⅔ of the voltage of the power supply is selected as a function of testing the pump 1 to provide accurate detection of the emitted electromagnetic radiation at the detector. At 616, the comparator generates a detection signal indicating whether the offset output signal exceeds the threshold. At 618, a controller of the pump 1 determines whether a compatible pump set 5 is loaded in the pump 1 as a function of the detection signal, which is a function of the output signal from the filter. If the controller determines that a pump set 5 is loaded in the pump 1 (e.g., IR emitted by the IR emitter 105 is received at the IR detector 109), at 620 the controller allows a pumping operation to begin. The controller may inform a user of the pump 1 that pumping operations are allowed via a user interface of the pump 1 such as display screen 9 at 626.

Ambient light contains a plurality of wavelengths of electromagnetic radiation. Sunlight continuously produces electromagnetic radiation of all wavelengths without any one wavelength being dominant. Fluorescent light sources produce relatively little IR, but electromagnetic radiation pulsed at about 60 Hz from incandescent light bulbs generally increases in intensity as the wavelength of electromagnetic radiation increases such that incandescent light sources produce an excess of IR. Therefore, ambient light produces IR interference at about 0 Hz and 60 Hz and filtering for another frequency (i.e., the predetermined frequency at which the emitted IR signal is pulsed) substantially reduces the effect of these noise sources.

With respect to visible light, sunlight continuously produces electromagnetic radiation in the visible range which can interfere with accurate visible light signal detection. Incandescent light sources produce visible light at about 60 Hz that generally increases in intensity as the wavelength of the visible light increases. Fluorescent light sources produce electromagnetic radiation at about 60 Hz in the visible range that is substantially more intense at certain wavelengths than at others. Both incandescent and fluorescent produce relatively little visible light at a wavelength of 510 nanometers (i.e., green light). Thus, visible light noise is reduced by emitting and detecting a visible light signal having a wavelength of 510 nanometers. Advantageously, further aspects of the invention substantially reduce the effect of these noise sources by filtering to exclude electromagnetic radiation at wavelengths other than 510 nanometers. Alternatively, or additionally, because sunlight produces non-pulsed visible light and fluorescent and incandescent light sources produce visible light pulsed at about 60 Hz, the effect of these noise sources can be substantially reduced by filtering at another frequency (i.e., the predetermined frequency at which the visible light signal is pulsed).

Figure 7A:
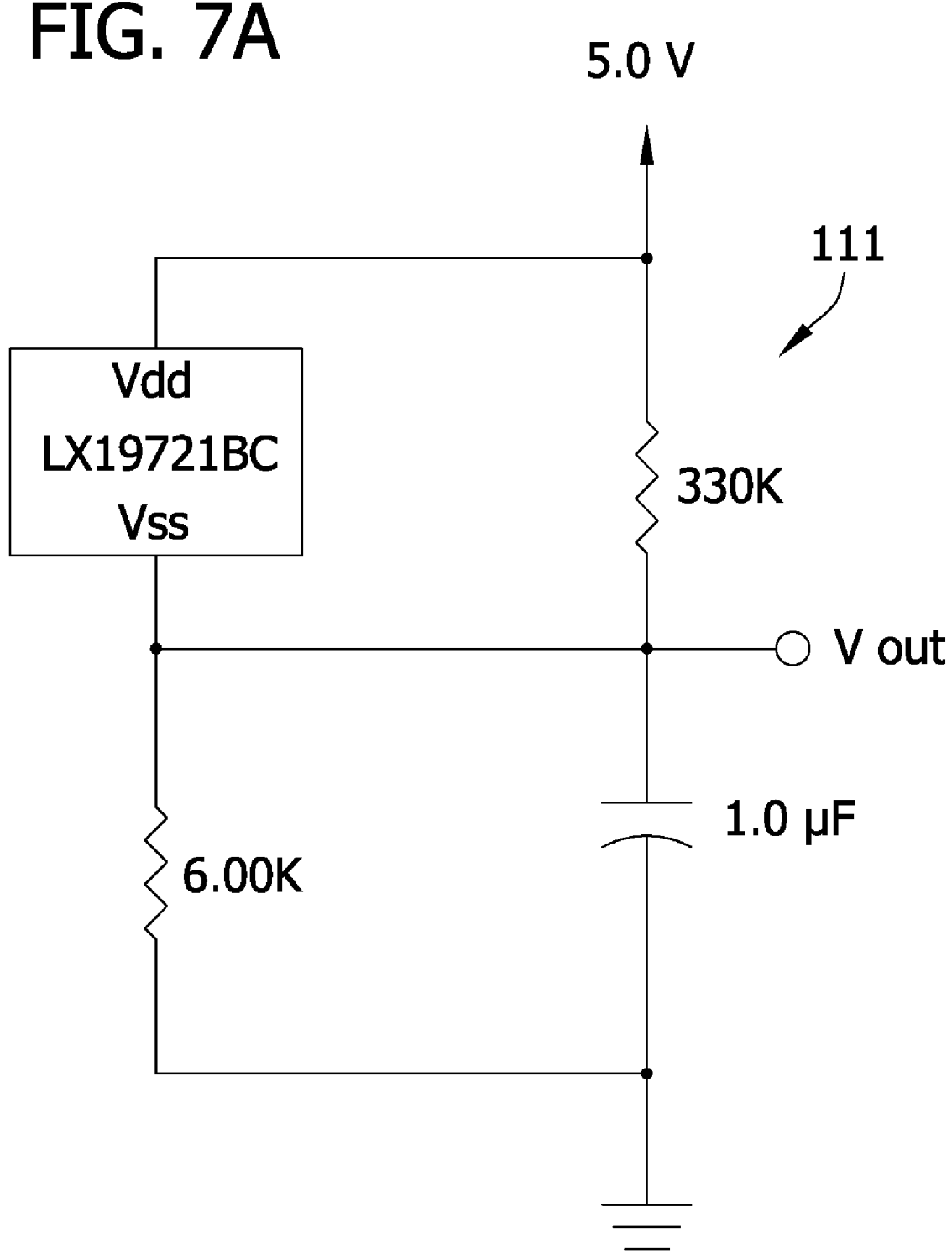
FIG. 7A is an exemplary schematic diagram illustrating a visible light detector circuit embodying aspects of the invention.

Electromagnetic radiation detectors have inherent wavelength response characteristics. In other words, varying wavelengths of electromagnetic radiation will affect the detector signal of a given detector to varying degrees. Typically, the response curve of a detector resembles a bandpass filter curve. For example, the detector signal of a visible light detector having a passband centered at about 510 nanometers is higher when exposed to green light at about 510 nanometers as compared to visible light at about 600 nanometers of the same amplitude. One example of a visible light detector centered at 510 nanometers is an LX1972 made by Microsemi of Garden Grove, Calif. FIG. 7A illustrates a visible light detector 111 according to an embodiment of the invention.

In one embodiment, the pump set 5 modifies IR by transmitting it to an IR detector, and the controller determines that a compatible pump set 5 is loaded in the pump 1 if the detection signal corresponds to an emitted IR signal. In another embodiment, the pump set 5 modifies visible light by blocking visible light, and the controller determines that a compatible pump set 5 is loaded in the pump 1 if the detection signal does not correspond to the emitted visible light. In yet another embodiment of the invention, the controller 504 must determine both that an emitted IR signal is being received at an IR detector and that an emitted visible light signal is being blocked from a visible light detector in order to determine that a compatible pump set 5 is properly loaded in the pump 1.

If the controller 504 determines that a compatible pump set 5 is not properly loaded, at 622, the controller prevents pumping operations. At 624, the controller 504 informs a user of the pump 1 that a compatible pump set 5 is not loaded in the pump 1 properly via an audible and/or visual alarm via a user interface of the pump 1 such as display screen 9.

In one embodiment of the invention, the controller 504 pulses the IR emitter 105 (see FIG. 5) until the IR detector 109 receives a signal recognizing that the safety interlock device 61 is loaded in the pump 1. Advantageously, filter 512 prevents electromagnetic radiation other than the pulsed IR from affecting the signal. Next, the visible light emitter 433 is activated to send a light signal that is blocked by the safety interlock device 61 if the safety interlock device is correctly loaded in the seat 91. The visible light detector 111 is operated to check for the visible light signal and to detect excess ambient light. If either condition is detected (i.e., light from emitter 433 or excess ambient light), the controller 504 activates an alarm that warns the user to check the alignment of the pump set 5 and does not allow the pump 1 to operate until the condition is corrected. The blockage of ambient light by the safety interlock device 61 causes the controller 504 to recognize that a compatible pump set 5 is properly loaded and the pump may be operated. The pump 1 detects a fault condition if the visible light detector 111 detects the visible light signal from the visible light emitter 433 after the IR detector 109 detects the presence of the safety interlock device 61.

Figure 8:
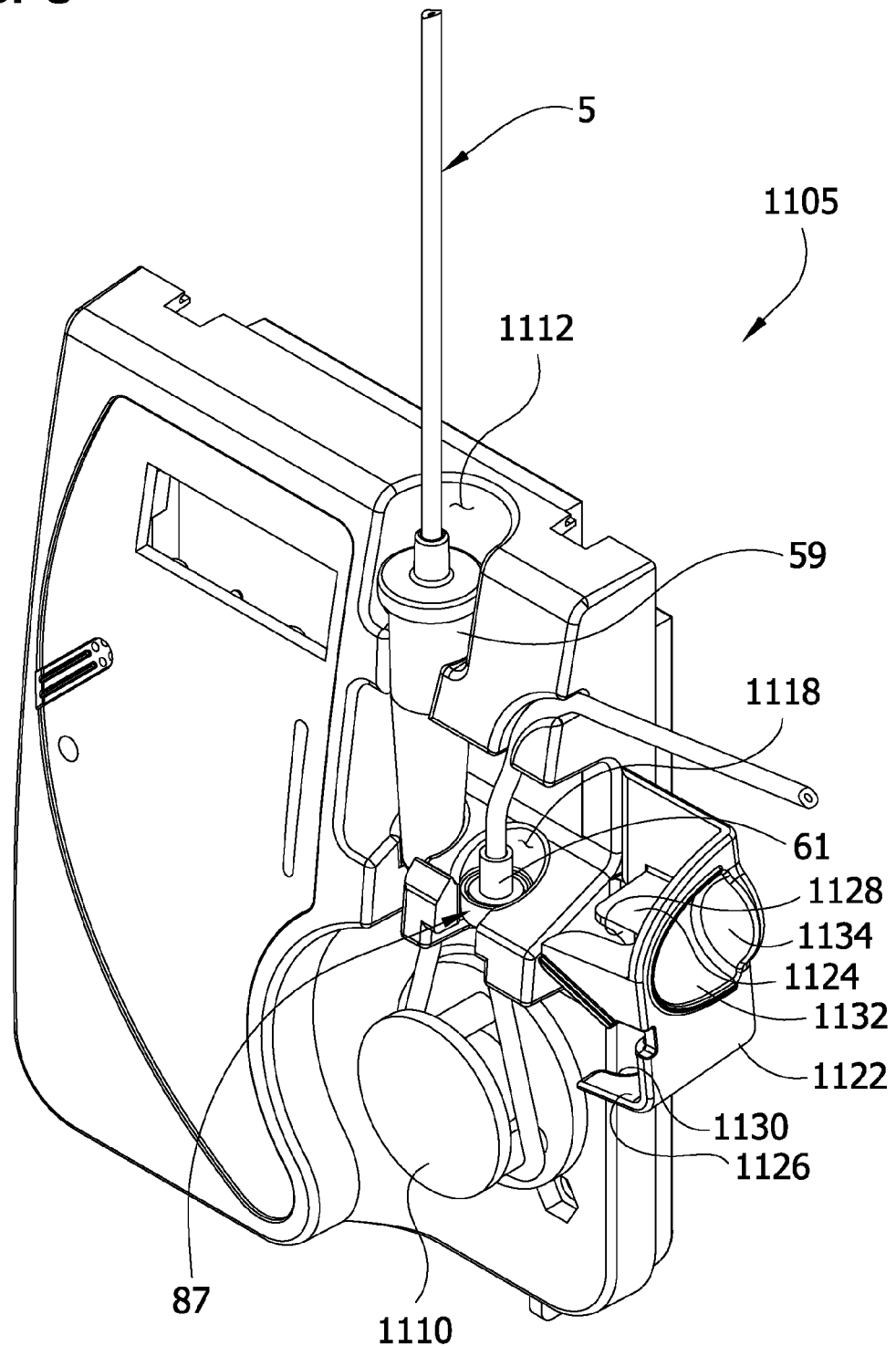
FIG. 8 is a perspective view of a pump having a cover in an open position.
Figure 9:
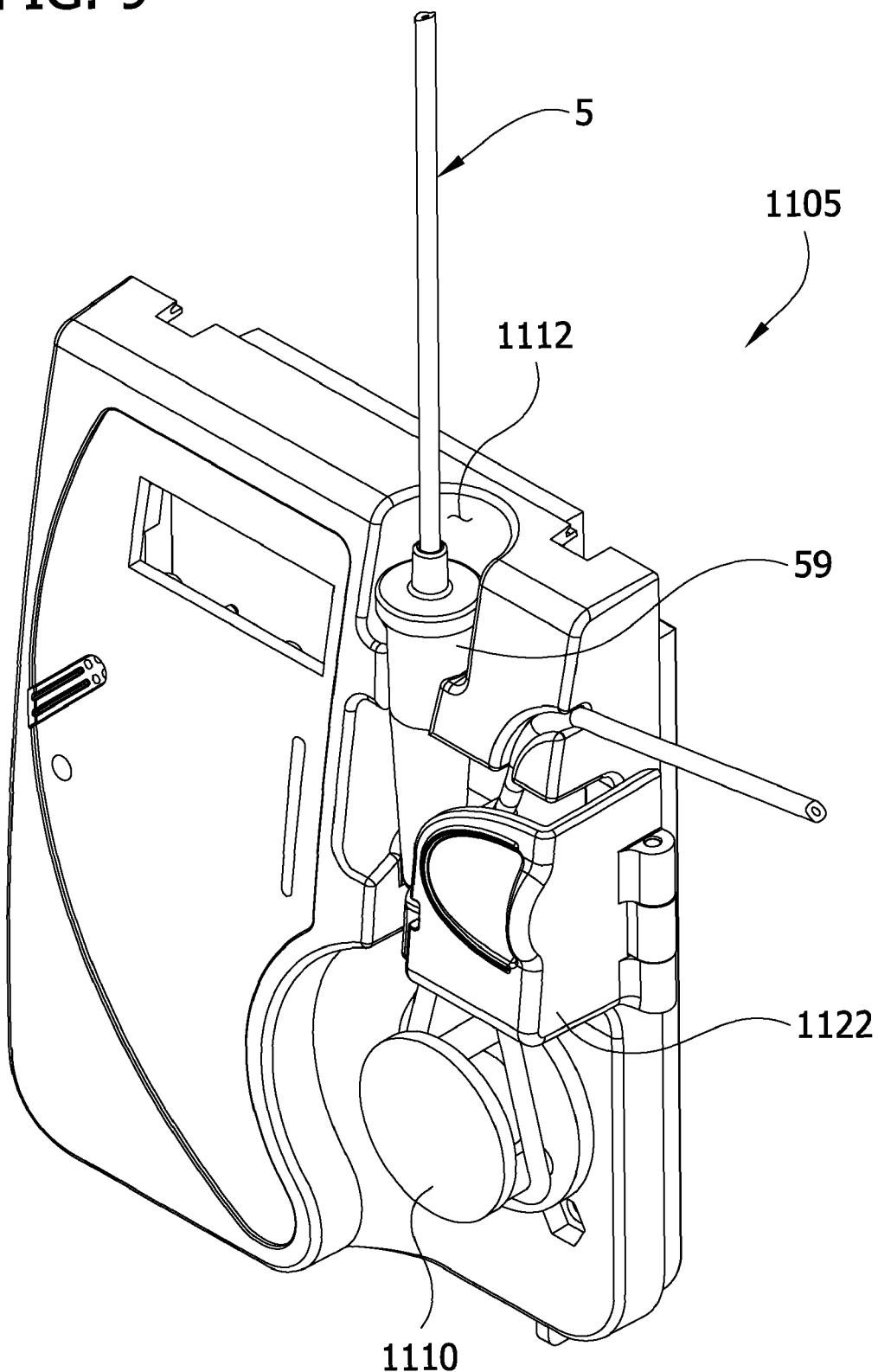
FIG. 9 is a perspective view of the pump of FIG. 8 with the cover in a closed position.

Referring now to FIGS. 8 and 9, an enteral feeding pump 1105 is shown with a cover 1122 in a generally open position according to another embodiment of the invention. The pump 1105 includes the pump rotor 37, a first recess 1112 for holding the drip chamber 59 of the pump set 5, and a second recess 1118 for holding a safety interlock device 61 of the pump set 5. The safety interlock device 61 has an electromagnetic radiation propagation affecting member 87. The pump set 5 also includes tubing wrapped around the pump rotor 37 and fluidly connecting the drip chamber 59 to the safety interlock device 61. The pump set 5 is removable from the pump 1105. The pump also includes the IR emitter 105, the IR detector 109, the visible light emitter 433, and the visible light detector 111. A controller of the pump 1105 (e.g., the controller 504 of the pump 1) determines whether a compatible pump set 5 is loaded in the pump 1105 as a function of input from the IR detector 109 and visible light detector 111 as described above. In one embodiment of the invention, operation of the IR emitter 105 and detector 109 and the visible light emitter 433 and detector 111 to determine whether a compatible pump set 5 is properly loaded is initiated by closing the cover 1122.

The cover 1122 is generally opaque such that it prevents the transmission of visible light to the visible light detector when the safety interlock device 61 is received in the second recess 1118. This allows the pump 1105 to operate in high ambient light scenarios while accurately determining whether the pump set 5 is properly loaded. The cover 1122 may be hinged to the pump 1105 so that it pivots between the open position (FIG. 8), whereby it does not cover the second recess 1118 so that the safety interlock device 61 may be received in or removed from the second recess, and a closed position (FIG. 9), whereby it substantially covers the entire safety interlock device 61 received in the second recess. The cover 1122 includes upper and lower arms 1124, 1126 having notches 1128, 1130 sized and shaped for receiving tubing associated with the safety interlock device in generally close-fitting relation when the cover is closed so as to substantially encase the safety interlock device 61 on all sides, thus blocking ambient light from the visible light detector when the safety interlock device is received in the second recess. The notches may be lined with an elastic material (not shown), such as rubber, so that tubes of different sizes may be snugly received in the notches to substantially encase the safety interlock device on all sides without pinching the tubes of the pump set 5 and causing occlusions. The cover 1122 (e.g., the upper arm 1124) may also aid in properly locating the safety interlock device 61 in the second recess 1118 as the cover is being closed. More specifically, the notch 1128 is sized so that the safety interlock device 61 cannot pass through the notch 1128. Thus the safety interlock device 61 is held down in the second recess 1118 by the upper arms 1124 when the cover 1122 is closed. The cover 1122, including the upper and lower arms 1124, 1126, may be formed such as by injection molding, as a single piece of material. The cover 1122 also includes a depression 1132 and a finger grip 1134 that can be easily grasped for opening and closing the cover 1122. It will be understood that a cover may have a different configurations within the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A medical pump for pumping fluid through a pump set loaded therein, said pump set being adapted for modifying electromagnetic radiation transmitted therethrough when properly loaded in the medical pump, said medical pump comprising:
an emitter for emitting electromagnetic radiation having a predetermined wavelength;
a detector for receiving electromagnetic radiation and providing a detector signal representative of the electromagnetic radiation received by the detector, said electromagnetic radiation received by the detector including the electromagnetic radiation having the predetermined wavelength emitted by the emitter and electromagnetic radiation having at least one wavelength other than the predetermined wavelength;
a filter circuit for filtering the detector signal provided by the detector into a portion of the detector signal representative of the electromagnetic radiation having the wavelength other than the predetermined wavelength and into another portion of the detector signal representative of the electromagnetic radiation having the predetermined wavelength, said filter circuit providing an output signal representative of the portion of the filtered detector signal representative of the electromagnetic radiation having the wavelength other than the predetermined wavelength; and
a controller for determining that a compatible pump set is properly loaded in the pump when the output signal is below a threshold and when the other portion of the detector signal represents that the electromagnetic radiation having the predetermined wavelength is not detected, said controller being configured to enable the pump for pumping when the compatible pump set is properly loaded in the pump.

2. The medical pump of claim 1 further comprising:
a second emitter for emitting electromagnetic radiation having a second predetermined wavelength different from the predetermined wavelength and from the at least one other wavelength;
a second detector for receiving electromagnetic radiation and providing a second detector signal representative of the intensity of the electromagnetic radiation received by the second detector, said electromagnetic radiation received by the second detector including the electromagnetic radiation having the second predetermined wavelength emitted by the second emitter; and
wherein the controller determines whether a compatible pump set is properly loaded in the pump as a function of the output signal and the second detector signal.

3. The medical pump of claim 1 wherein the pump set comprises an electromagnetic radiation propagation affecting member for substantially blocking the detector from receiving the emitted electromagnetic radiation when the pump set is properly loaded in the pump, and wherein the controller is responsive to the portion of the output signal representative of the electromagnetic radiation having the wavelength other than the predetermined wavelength being less than the threshold for enabling the pump for pumping.

4. The medical pump of claim 1 further comprising a user interface responsive to the controller for notifying a user that a pump set loaded in the pump is not compatible with the pump or is not properly loaded in the pump as indicated by the output signal.

5. The medical pump of claim 1 wherein the controller comprises:

an amplifier for amplifying the output signal; and
an offset circuit for referencing the amplified output signal to about half of a voltage of a power supply of the medical pump.

6. The medical pump of claim 1 wherein the predetermined wavelength of the electromagnetic radiation is approximately 510 nanometers.

7. The medical pump of claim 2 wherein the second emitter is pulsed at a predetermined frequency; and further comprising:
a second filter circuit for filtering the second detector signal provided by the second detector to exclude frequencies other than the predetermined frequency such that the second detector signal is representative of the intensity of the electromagnetic radiation pulsed at the predetermined frequency received by the second detector.

8. The medical pump of claim 7 wherein the controller further comprises a comparator for comparing the output signal to the threshold for determining whether a compatible pump set is properly loaded in the pump, wherein the threshold of the comparator is about $2/3$ of the voltage of the power supply of the medical pump, and wherein the filter circuit is a bandpass filter.

9. The medical pump of claim 8 wherein the bandbpass filter is a Bessel type bandpass filter.

10. A method of determining whether a compatible pump set is properly loaded in a medical pump, said pump set modifying electromagnetic radiation transmitted therethrough when properly loaded in the pump, said method comprising:
emitting, by an emitter of the pump, pulses of electromagnetic radiation through a portion of a pump set loaded in the pump, said electromagnetic radiation having a predetermined wavelength and being pulsed at a predetermined frequency;
receiving electromagnetic radiation at a detector of the pump, said electromagnetic radiation received at the detector including the electromagnetic radiation having the predetermined wavelength and electromagnetic radiation having at least one wavelength other than the predetermined wavelength, wherein the detector provides a detector signal representative of the received electromagnetic radiation;
filtering, via a filter circuit of the pump, the detector signal into a portion representative of the pulses of electromagnetic radiation having the predetermined frequency and the predetermined wavelength and into another portion representative of the electromagnetic radiation having the at least one other wavelength, said filter circuit providing an output signal representative of the intensity of the other portion representative of the electromagnetic radiation having the at least one other wavelength received by the detector;
comparing the output signal to a threshold;
determining whether the portion of the detector signal representative of the pulses of electromagnetic radiation having the predetermined frequency and the predetermined wavelength is detectable; and
determining whether the pump set is compatible with the pump and properly loaded in the pump as a function of said comparing when the other portion of the detector signal represents that the electromagnetic radiation having the predetermined wavelength is not detected.

11. The method of claim 10 further comprising:
emitting, by a second emitter of the pump, second electromagnetic radiation through a portion of a pump set loaded in the pump, said second electromagnetic radiation having a second predetermined wavelength different from the predetermined wavelength and from the at least one other wavelength;

receiving electromagnetic radiation including the second electromagnetic radiation having the second predetermined wavelength at a second detector of the pump and providing a second detector signal representative of the received electromagnetic radiation;

comparing the second detector signal to a second threshold to determine whether the emitted second electromagnetic radiation transmitted through the pump set has been modified; and generating a second detection signal representative of the comparison of the second detector signal to the second threshold; and wherein determining whether the pump set is compatible with the pump and properly loaded in the pump is further a function of the second detection signal.

12. The method of claim 10 further comprising substantially blocking electromagnetic radiation transmitted through the pump set from reaching the detector of the pump when the pump set is properly loaded in the pump, and wherein generating the detection signal is responsive to the output signal being less than the threshold.

13. The method of claim 10 further comprising:
amplifying the output signal; and
referencing the amplified output signal to about half of a voltage of a power supply of the pump; and
wherein the threshold is about ⅔ of the voltage of the power supply of the pump, and wherein filtering comprises filtering with a bandpass filter.

14. The method of claim 10 wherein the predetermined wavelength of the electromagnetic radiation is approximately 510 nanometers; and the predetermined frequency is approximately 1 kHz.

15. The method of claim 11 wherein emitting further comprises pulsing the second electromagnetic radiation at a second predetermined frequency; and further comprising:
filtering the provided second detector signal to exclude frequencies other than the second predetermined frequency such that said second detector signal is representative of the intensity of the electromagnetic radiation pulsed at the second predetermined frequency received by the second detector.

16. A medical pump for pumping fluid through a pump set loaded therein, said pump set comprising a safety interlock device that is transmissive to IR electromagnetic radiation and substantially opaque to visible light, said medical pump comprising:
an infrared (IR) emitter for emitting pulses of IR electromagnetic radiation, said IR electromagnetic radiation having a predetermined wavelength and said pulses having a predetermined frequency;
an IR detector for receiving electromagnetic radiation and providing an IR detector signal representative of the received electromagnetic radiation;
a filter circuit for filtering the IR detector signal provided by the IR detector to exclude frequencies other than the predetermined frequency of the pulses of IR electromagnetic radiation having the predetermined wavelength, said filtered IR detector signal being representative of the intensity of the IR electromagnetic radiation transmitted through the safety interlock device and received by the IR detector;
a visible light emitter for emitting visible light having at least one wavelength other than the predetermined wavelength;
a visible light detector for receiving electromagnetic radiation and providing a visible light detector signal representative of the received electromagnetic radiation; and
a controller for determining that a compatible pump set is properly loaded in the pump when the filtered IR detector signal indicates that the IR detector received the pulses of IR electromagnetic radiation having the predetermined wavelength emitted by the IR emitter and transmitted through the safety interlock device and when the visible light detector signal indicates that the safety interlock device blocked the visible light detector from receiving the visible light emitted by the visible light emitter, said controller being configured to enable the pump for pumping when the compatible pump set is properly loaded in the pump.

17. A method of determining whether a compatible pump set is properly loaded in a medical pump, said pump set modifying electromagnetic radiation transmitted therethrough when properly loaded in the pump, said method comprising:
emitting, by an emitter of the pump, infrared (IR) electromagnetic radiation having a predetermined wavelength through a portion of a pump set loaded in the pump;
detecting, by a detector of the pump, electromagnetic radiation including IR electromagnetic radiation having the predetermined wavelength and visible light having at least one wavelength other than the predetermined wavelength, wherein the detector provides a detector signal representative of the detected electromagnetic radiation;
filtering, by a filter circuit of the pump, the detector signal to exclude a portion of the detector signal representative of the visible light having the at least one wavelength other than the predetermined wavelength from another portion of the detector signal representative of the IR electromagnetic radiation having the predetermined wavelength, said filter circuit providing an output signal representative of the filtered detector signal;
comparing the output signal to an IR threshold to determine whether the emitted IR electromagnetic radiation has been transmitted through the pump set;
comparing the output signal to a visible light threshold to determine whether the pump set has substantially blocked visible light from the detector; and
determining that the pump set is compatible with the pump and properly loaded in the pump as a function of said comparing when the IR electromagnetic radiation detected by the detector exceeds the IR threshold and the visible light detected by the detector does not exceed the visible light threshold.

\* \* \* \* \*